United States Patent [19]

Weil

[11] 4,364,745
[45] Dec. 21, 1982

[54] PLANT HYDROCARBON RECOVERY PROCESS

[75] Inventor: Thomas A. Weil, Naperville, Ill.

[73] Assignee: Standard Oil Company (Indiana), Chicago, Ill.

[21] Appl. No.: 277,836

[22] Filed: Jun. 26, 1981

[51] Int. Cl.³ ............................................. C10J 3/00
[52] U.S. Cl. ....................................... 48/209; 585/240; 201/2.5; 201/8; 201/25
[58] Field of Search ............... 48/209, 197 R, 206; 201/2.5, 25, 8; 585/240, 733

[56] References Cited

U.S. PATENT DOCUMENTS

| | | | |
|---|---|---|---|
| 2,080,767 | 5/1937 | Dreyfus | 585/539 |
| 3,148,227 | 9/1964 | Hearon et al. | 585/240 |
| 3,840,354 | 10/1974 | Donath | 48/206 |
| 3,846,096 | 11/1974 | Mallan et al. | 48/209 |
| 3,864,100 | 2/1975 | Blaskowski | 48/197 R |
| 4,278,446 | 7/1981 | Rosenberg, Jr. et al. | 48/197 R |
| 4,313,011 | 1/1982 | Weil et al. | 48/209 |

Primary Examiner—S. Leon Bashore, Jr.
Assistant Examiner—Michael L. Goldman
Attorney, Agent, or Firm—William C. Clarke; William T. McClain; William H. Magidson

[57] ABSTRACT

Process for production and recovery of fuel gases and organic liquids from biomass by use of an upflow furnace, wherein said biomass is preheated at a temperature of from 100° C. to 1500° C. and thermally converted at a temperature of from 200° C. to 1000° C. in a reducing atmosphere.

8 Claims, 2 Drawing Figures

PLANT HYDROCARBON RECOVERY PROCESS

BACKGROUND OF THE INVENTION

This invention relates generally to a process for the production and recovery of hydrocarbon chemical feedstocks and hydrocarbon fuels from renewable plant sources using whole plants and extracts from whole plants. This invention in particular relates to the rapid and direct conversion of such materials by a process requiring hydropyrolysis in the gas phase.

Considerable evidence in the literature suggests that products initially formed during thermal decomposition of carbonaceous materials are largely in the liquid molecular weight range and that these products decompose, crack to gases and recombine at a rapid rate to form refractory products such as coke the longer they are subjected to the thermal decomposition conditions. Lifetime of the liquid products is also short, as is indicated by available evidence. Therefore, in order to maximize liquid yields from such decompositions, it is desirable to limit the time during which the products initially formed are subject to the decomposition conditions. Thus a low residence time of the carbonaceous material in the thermal decomposition zone and a high rate of decomposition are desirable. Similarly, thermal decomposition of carbonaceous materials in a reducing atmosphere and at low pressures facilitates the escape of volatile products from the carbonaceous material and from one another and minimizes the tendency to recombine. Also, it is generally recognized that in thermal decomposition of carbonaceous materials rapid quenching of the decomposition reactions and/or reaction of the liquid products with a stabilizing material such as hydrogen maximizes production of the liquid products. If rapid quenching does not take place or if sufficient stabilizing material is not available, some of the free radical decomposition products will polymerize to form unreactive char.

Thermal decomposition of carbonaceous materials to obtain hydrocarbon products can be effected by direct heating in the presence or absence of oxygen. The presence of oxygen causes the reactor product to contain greater or lesser amounts of carbon oxides. For example, Brink, et al., U.S. Pat. No. 3,639,111 teaches a method and apparatus for distilling organic wastes at an elevated temperature and in the presence of a controlled amount of oxygen insufficient for complete combustion, the elevated temperature being above a critical temperature zone, thereby reducing or cracking gases from the material to hydrogen, carbon monoxide and methane. Brink, et al., U.S. Pat. No. 3,718,446 teaches the pyrolysis of organic materials from pulping operations in the presence of limited oxygen at a sufficiently high temperature (of 800° C. to 1,200° C. or higher) and for a sufficient length of time (of from 1 to 30 seconds) to prevent recombination reactions and produce stable products such as phenols, hydrogen, carbon monoxide, carbon dioxide and methane. Anderson, U.S. Pat. No. 3,729,298 teaches a process for disposing of carbonaceous refuse by thermally decomposing it in a shaft furnace with temperatures on the order of 3000° F. and simultaneously producing a fuel or synthesis gas primarily containing over 50% carbon monoxide by combusting the char and hydrogen. A gas containing at least 40% oxygen is fed into the furnace to create a thermal driving force in excess of 1600° F. A low rate of oxygen introduction is taught to maintain a reducing atmosphere in the hearth to prevent overoxidation of the char to $CO_2$ and oxidation of the metallic components of the refuse although the process can be operated under mildly oxidizing conditions.

If an oxygen source is not used to maintain direct combustion, an indirect method of heating typically is used which reduces formation of carbon oxides but requires other sources of energy input. Heat transfer, and therefore the efficiency of the process, can be accordingly diminished. For example, Grannen, et al., U.S. Pat. No. 3,843,457 teaches a process for microwave pyrolysis of organic materials to recover vaporizable organic compounds such as organic acids and aldehydes from nominally solid organic wastes by comminuting the wastes and mixing them with a gas stream at a pressure substantially less than atmospheric. The gases are preferably reducing gases, particularly hydrogen. The comminuted wastes are subject to microwave discharge which effects molecular decomposition and the vaporized components are thereby removed from the gas stream. Fleming, U.S. Pat. No. 4,002,438 teaches a method and a device for the flash pyrolytic conversion of organic materials into gaseous or liquid fuels comprising methane, hydrogen, ethane with some light oil fractions in a single self-contained vessel wherein problems of clogging, coke formation, and sludge formation are substantially avoided by use of a mixture of dense, hard abrasion-resistant material which is recycled with recycled product gas and combustion air. Choi, et al., U.S. Pat. No. 4,078,973 teaches a closed loop pyrolysis process for organic solid wastes wherein the heat is supplied by inert particles which are heated in a separate combustion zone. The residence time during pyrolysis is generally less than 10 seconds. The pyrolysis temperature is between 600° F. and the introduction temperature of the inert particles. The pyrolysis zone can be between 600° F. to about 2,000° F. The carrier gases are oxygen-free. The products are carbon-containing char, pyrolytic oils of an oxygenated nature and gases primarily of the oxides of carbon and light hydrocarbons. Garrett, et al., U.S. Pat. No. 4,153,514 teaches a process for recovery of chemical values from waste solids wherein shredded waste solids of a 0.25 inch maximum dimension are intermixed with hot char and a carrier gas and passed through a pyrolysis zone under turbulent conditions at temperatures of from 300° F. to 2000° F. The maximum particle size is critical because larger sizes do not provide the high rate of heat transfer essential to the process.

Processes have been disclosed for recovering liquids from carbonaceous solids and lower boiling liquids from higher boiling liquid hydrocarbons which involve a rapid decomposition of the carbonaceous material in the presence of hydrogen and at a low pressure and a rapid quenching of the decomposition reaction. However, rapid decomposition at low pressure and rapid quenching entails the problems of feeding the material into the reactor and removing it readily.

In particular, Greene, U.S. Pat. No. 3,997,423 discloses a process of producing carbonaceous tars from liquid or crushed solid carbonaceous material comprising (1) introducing carbonaceous material into a reactor; (2) adding hot hydrogen to the carbonaceous material in the reactor; (3) reacting the hydrogen and carbonaceous material for a period of from about two milliseconds to about two seconds at a temperature of about 400° C. to 2,000° C. and at a pressure between atmospheric and 250 psia.; and (4) quenching the mixture within the reactor, with the total residence time for steps (2) and (3) varying from about two milliseconds to about two seconds. The patentee states that the heat-up rate of the carbonaceous material is in excess of 500° C. per second.

Greene, U.S. Pat. No. 4,012,311 discloses a process which is similar to the process of Greene, U.S. Pat. No. 3,997,423 and in which the decomposition reaction takes place at a pressure between atmospheric and 450 psia.

Pelofsky et al., U.S. Pat. No. 4,003,820 disclose a process which is similar to the process of Greene, U.S. Pat. No. 3,997,423, and in which the decomposition reaction takes place at a higher pressure between 500 and 5,000 psig.

Although Pelofsky et al., U.S. Pat. No. 4,003,820 and Greene, U.S. Pat. No. 4,012,311 do disclose in general terms an additional step in which the carbonaceous material is pretreated with hydrogen prior to being decomposed, such patents do not disclose the conditions of such pretreatment.

Furthermore, none of Greene, U.S. Pat. Nos. 3,997,423; 4,012,311; and Pelofsky, U.S. Pat. No. 4,003,820 disclose a suitable method for rapidly introducing the carbonaceous material into the reactor. These patents disclose only that, in order to overcome the reactor pressure, both the carbonaceous material and the incoming hydrogen must be fed into the reactor at a pressure exceeding that of the reactor. Rapid passage of the carbonaceous material into and through the reactor is essential if a short decomposition time and a commercially acceptable, high through-put of carbonaceous material is to be achieved.

One suitable method for rapidly introducing the carbonaceous material into the decomposition zone involves entraining the carbonaceous material in a stream of compressed gas and instantaneously expanding and accelerating this stream as it passes through a restricted area into the decomposition zone. A similar technique is employed in a method for disintegrating coal solids as disclosed in Yellott, U.S. Pat. No. 2,515,542. Such technique not only serves to introduce the carbonaceous material rapidly into the decomposition zone but also permits the volatile fragments and radicals which form in the interior of the carbonaceous material to move rapidly away from the carbonaceous material and from one another.

Avco Everett Research Laboratory, Inc. has in very general terms disclosed to various people in the industry a coal gasification technique utilizing a two-stage gasifier. In the first stage, char is burned with oxygen to generate heat. The combustion gases from this combustion are then fed to a pyrolyzer through a converging-diverging nozzle. A large pressure drop is maintained across the nozzle. The combustion gases are accelerated to sonic conditions in the converging section of the nozzle, resulting in a cooling of the gases. Coal and steam are fed or aspirated into the stream of combustion gases at or slightly upstream of the throat of the nozzle. The mixture is then accelerated to supersonic flow in the diverging section of the nozzle and discharges into the pyrolyzer as a confined jet. As the gas velocity decreases from supersonic flows to subsonic flow in the pyrolyzer, a shock occurs which results in rapid heating of the coal, leading to the rapid formation of volatile material in the coal. Many of the volatiles are believed to be free radicals which are stabilized by the steam, thus preventing soot formation. Argon, carbon monoxide, helium and nitrogen have also been studied as stabilization gases. The residence time of the reaction mixture in the pyrolyzer is about 40 milliseconds.

OBJECTS OF THE INVENTION

It is therefore a general object of the present invention to provide an improved method for recovering more valuable products from carbonaceous biomass material which possesses the aforementioned desirable features and overcomes the shortcomings of previous methods.

More particularly, it is an object of the present invention to provide a thermal decomposition method for recovering liquids and gases from biomass carbonaceous material which maximizes liquid yields during the time which the carbonaceous material is subjected to thermal decomposition conditions.

Another object of the present invention is to provide a method for decomposing biomass carbonaceous material which maximizes the liquid yields by facilitating the escape of volatile products from the carbonaceous material and from one another and thereby minimizes their tendency to recombine.

A further object of the present invention is to provide an efficient method for decomposing biomass carbonaceous materials which enhances the accessibility of the volatile products initially formed from the carbonaceous material to an environment of stabilizing material.

A further object is to provide a suitable method for introducing the biomass material into the reactor and a suitable method of removing the products of the thermal decomposition.

Other objects and advantages of the invention will become apparent upon reading the following detailed description and appended claims, and upon reference to the accompanying drawing.

SUMMARY OF THE INVENTION

A process for production and recovery of fuel gases and organic liquids from hydrocarbon-containing whole plants and plant extracts which are suitable for use as chemical feedstocks or as fuels wherein plant biomass or plant extract is thermally converted in an upflow furnace in a reducing atmosphere at a temperature within the range from about 200° C. to 1000° C. for 0.1 second to one minute, the resulting liquid and gaseous hydrocarbons being stabilized in an atmosphere of hydrogen and recovered in a condition suitable for use as chemical feedstocks or as hydrocarbon fuels.

DETAILS OF THE INVENTION

The invention relates to a process for producing and recovering fuel gases and organic liquids from whole plants which are rich in hydrocarbons. Examples of these plants are *Euphorbia heterophylla, Euphorbia lathyrus, Euphorbia marginata, Euphorbia tirucalli, Asclepias syriaca, Asclepias tuberosa, Grindelia squarrosa, Calotropis procera, Eucalyptus cineria* and *Apocynum sibiricum*. The invented process is not limited to these plants and can be applied to any hydrocarbon-containing plant including those in the Euphorbiaceae, Apocynaceae, Asclepiadaceae, Compositae, Myrtaceae and Pinaceae families.

The present invention is directed to a process for the thermal conversion of biomass in a reducing atmosphere at 200° C. to 1000° C. wherein increased yields of liquid and gaseous hydrocarbons are obtained. The reducing atmosphere is obtained and sustained by the presence of hydrogen. Excess oxidation of the hydrocarbon products to less valuable materials is controlled by the presence of the reducing atmosphere and control of oxygen input. The liquid and gaseous hydrocarbons produced can be used as fuel gases or as feedstocks for chemical manufacture. The excess char is removed to serve as fuel or for hydrogen generation.

The thermal conversion zone reactions are moderated and controlled by the amount of hydrogen introduced into the furnace and the amount of oxygen which is introduced into the heating zone. Essential elements of the invented process are that an excess of hydrogen over oxygen be present in the furnace in a mole ratio of from about 2:1 to 100:1, hydrogen to oxygen and that minimal oxygen be present in the thermal conversion zone. Excess quantities of oxygen over the amount required to obtain the required temperature in the oxidation zone will diminish or eliminate the reducing atmosphere and affect the yield of desired products adversely. An excess of hydrogen is essential to maintain the hydrogen atmosphere and to stabilize the liquid products initially formed.

The thermal conversion zone reactions are obtained by subjecting the oxidation products to hydrogen, biomass feed, including whole plant biomass and biomass extract and a temperature of from about 200° C. to about 1000° C. Low residence time of the product in the thermal conversion zone is obtained by controlling the flow rate of hydrogen and by adjusting reactor size. Thermal conversion zone reactions are quenched by rapid expansion of the reaction mixture, causing a rapid drop in product temperature. Residence time in the thermal conversion zone of the upflow furnace is from about 0.1 second to about one minute.

Figure 1:
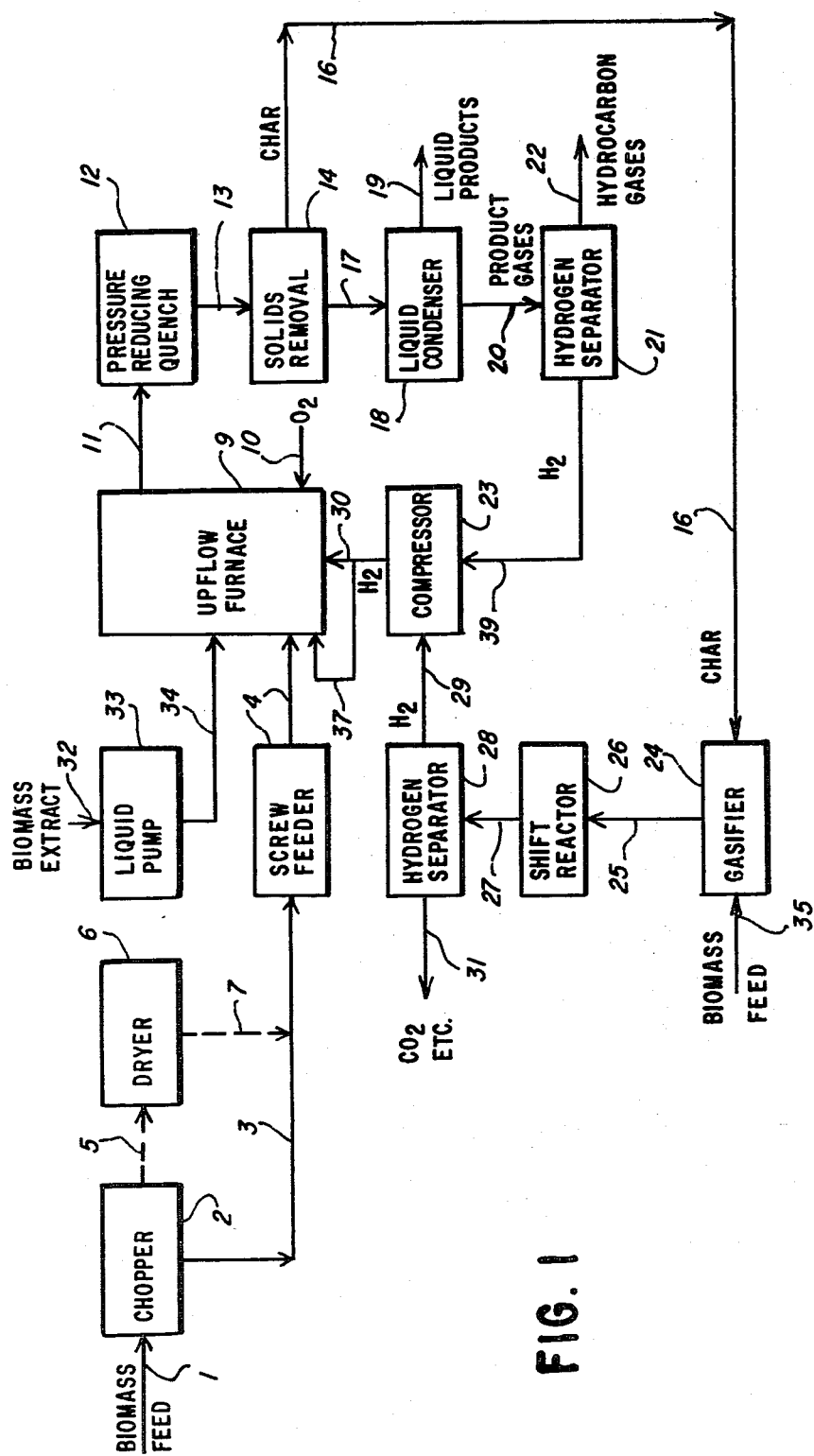
FIG. 1 is a schematic illustration of the invention according to which the biomass is thermally converted in a reducing atmosphere to produce gases such as methane, ethane, acetylene, ethylene, butene, other hydrocarbons, carbon monoxide, etc., and liquids composed of aliphatic, aromatic, olefinic, and functionalized compounds containing nitrogen and oxygen.

Referring to FIG. 1, the whole plant biomass is introduced by line 1 to the chopper or grinder 2. Chopped material is fed by line 3 to a reactor feeder system comprising a screw feeder 4. Alternatively, the chopped material is fed by line 5 to dryer 6 and thence by line 7 to screw feeder 4 by line 3. Entry to upflow furnace 9 by the chopped biomass is through the biomass screw feeder or other suitable means to maintain the pressure differential in upflow furnace 9. Entry of biomass extract is through a liquid pump 33 which is fed by line 32. Line 34 conveys the liquid biomass extract to upflow furnace 9. Biomass extract can be at ambient temperature or heated to a suitable temperature to about 200° C. to obtain liquid flow. The chopped biomass encounters the drying and preheating zone of upflow furnace 9 wherein a reducing atmosphere is present at a temperature within the range of from about 100° C. to about 1500° C. upon entry into upflow furnace 9. Air entry into upflow furnace 9 is restricted by the compacting in the screw feeder 4 or by the liquid pump 33. Positive pressure is maintained within the body of upflow furnace 9, thus maintaining the reducing atmosphere. An oxygen-containing gas is fed to the furnace by line 10 at a pressure of from 1 to 100 atmospheres. The dried and heated biomass or liquid extract is swept into the thermal conversion zone of upflow furnace 9 wherein steam and oxygen from oxidation zone of the furnace are present at a temperature within the range of from 200° C. to 1000° C. The hot hydrogen gas and product steam from the oxidation zone rise and are contacted with feed. Gas and liquid products plus any solids present are swept by line 11 to pressure reducing quench vessel 12 and thereupon transferred by line 13 to solids removal means 14, such as a cyclone. Char is removed by line 16 to gasifier 24 wherein biomass from line 35 and char from line 16 are gasified under suitable conditions. Upflow furnace liquid and gaseous products are removed by line 17 to liquids condenser 18, liquid products being removed by line 19. Product gases are transferred by line 20 to hydrogen separator 21 wherefrom product hydrocarbon gases are removed by line 22. Hydrogen from separator 21 is transferred to compressor 23 by line 39. Gas products from biomasss and char gasified in gasifier 24 are transferred by line 25 to shift reactor 26 and thence by line 27 to hydrogen separator 28. Hydrogen from separator 28 is fed to compressor 23 from whence it is fed under pressure to upflow furnace 9 by lines 30 and 37 at a pressure of from 1 to 100 atmospheres. Carbon dioxide and gases other than hydrogen are removed from separator 28 by line 31.

Figure 2:
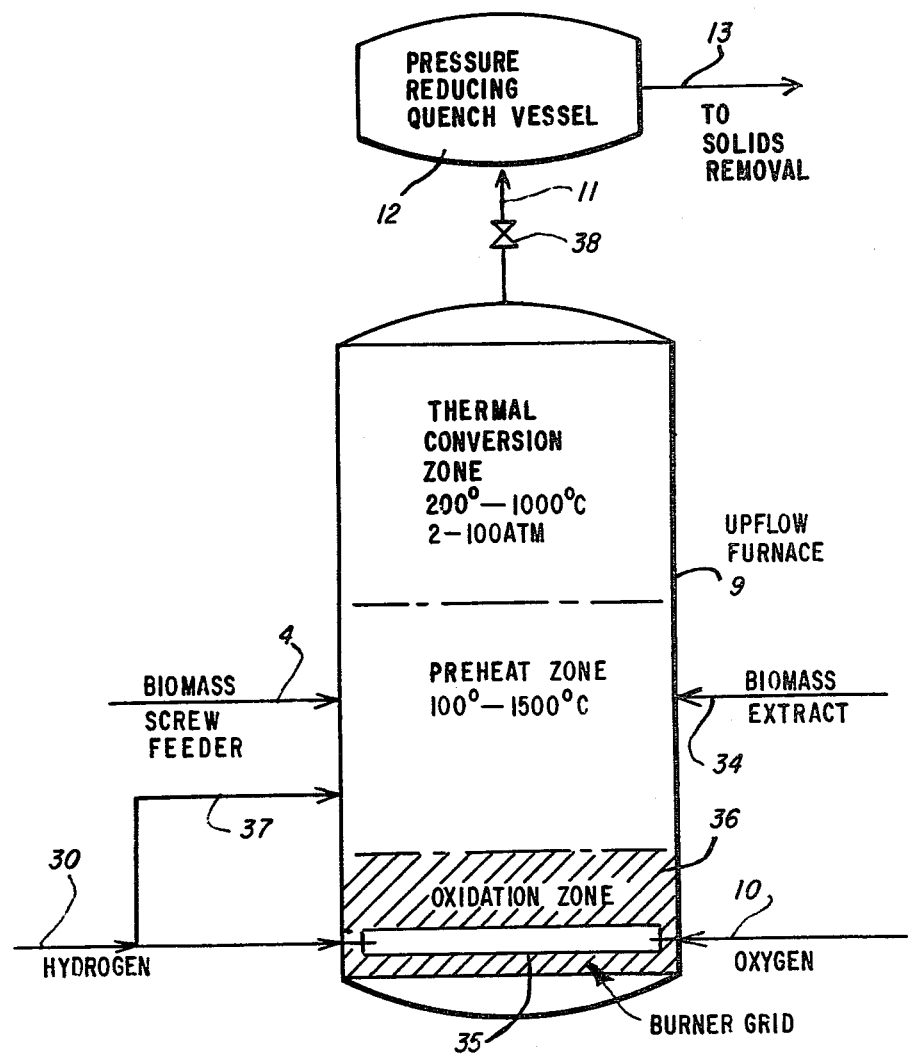
FIG. 2 depicts an up-flow furnace wherein the thermal reactions occur.

Referring to FIG. 2, hydrogen under pressure is fed into upflow furnace 9 by lines 30 and 37. Oxygen is fed into upflow furnace 9 by line 10. Burner grid 35 comprises a portion of oxidation zone 36 wherein the oxygen and hydrogen reaction takes place. Hydrogen from line 30 is also injected into upflow furnace 9 by line 37 into the preheat zone, thus maintaining the reducing atmosphere. Biomass is fed by screw feeder 4 into the body of the upflow furnace 9 in the preheat zone with means provided to exclude oxygen-containing gases from the inlet port. Positive pressure is maintained within the body of the upflow furnace 9 by compacting of the bulk biomass by the screw feeder. Dismembering of the compressed biomass bulk within the upflow furnace body is accomplished by passive shredders mounted within the furnace over the screw feeder orifice. Biomass extract is fed into the preheat zone by line 34, being atomized upon entry into the furnace. Product gases and hydrogen convey any unconverted biomass, gaseous and liquid products in an upflow movement through the thermal conversion zone to line 11. Pressure let-down valve 38 maintains required positive pressure within upflow furnace 9. Pressure reducing and temperature quenching vessel 12 causes a rapid temperature drop of product gases because of rapid expansion. Because of the high velocities generated through the pressure let-down valve, erosion of the valve body and seat can occur. Alloys of erosion-resistant materials are required for continued operational life.

The preheat zone temperature of upflow furnace 9 is within the range of from about 100° C. to about 1500° C. The thermal conversion zone temperature is within the range of from about 200° C. to about 1000° C. A positive pressure differential is maintained within the upflow furnace relative to the exterior of the upflow furnace with excess hydrogen at a pressure of from about 2 to about 100 atmospheres, to prevent entry of air into the furnace and to maintain the reducing atmospheres in the preheating and thermal conversion zones.

The present invention accordingly is directed to a process for the thermal conversion of biomass and biomass extract in a reducing atmosphere wherein increased yields of liquid and gaseous hydrocarbons are obtained from whole plants which contain hydrocarbons at a temperature within the range from about 200° C. to about 1000° C.

Particle size of biomass is not a critical element as particle size can range from finely divided particles to those of ½ inch and greater in size, with a median range of from about ¼ to ½ inch in length. Liquid plant extract can be fed into the furnace at room temperature or at a temperature wherein the liquid extract flows easily. It is not necessary to vaporize the extract as it can be atomized to be sprayed into the upflow furnace.

Although non-hydrocarbon containing plants can be used as the feed biomass, it is preferred that hydrocarbon containing plants selected from the group consisting of *Euphorbia heterophylla, E. lathyrus, Grindelia squarrosa, E. tirucalli, E. marginata, Eucalyptus cineria, Asclepias syriaca, Asclepias tuberosa, Calotropis procera* and *Apocynum sibiricum* and other hydrocarbon-producing plants in the Euphorbiaceae, Apocynaceae, Asclepiadaceae, Compositae, Myrtaceae and Pinaceae families be utilized as the feed material. Substantially larger quantities of liquid hydrocarbons and gases are produced from these hydrocarbon-containing plants than from non-hydrocarbon containing plants by the invented process.

Condensable liquids obtained in thermal conversion of hydrocarbon-containing whole plants and plant extracts are complex mixtures of at least 50 components. They are composed of aliphatic, aromatic, olefinic and functionalized compounds containing oxygen and nitrogen. In general, these functionalized organic liquids are soluble in solvents of moderate polarity and are less soluble in very polar or nonpolar solvents. Elemental composition of organic liquids obtained in thermal conversion of hydrocarbon-containing whole plants (e.g., *E. marginata, E. lathyrus* and *C. procera*) has been determined as being as follows: carbon 70–84 (wt)%; hydrogen 5.9–6.8 (wt)%; oxygen 10–17 (wt)%; nitrogen 2.0–4.1 (wt)%. In contrast to the above analyses, non-hydrocarbon-containing (i.e., non-latex containing) whole plants (e.g., sudangrass) have been analyzed as follows: carbon 56 (wt)%; hydrogen 7.6 (wt)%; oxygen 31 (wt)%, and nitrogen 1.2 (wt)%.

An essential element of this invention is an upflow furnace wherein the biomass feed is exposed to temperatures of from 200° C. to about 1000° C. in the thermal conversion zone for a period of from about 0.1 second to one minute, preferably for a period sufficiently short enough to stabilize the hydrocarbons contained in the plants more as liquids and less as gaseous products. The furnace is defined as an upflow type furnace wherein combuation of hydrogen preferably with oxygen, and less preferably with air, supplies precisely the amount of heat required for thermal conversion and recovery of the hydrocarbons contained in the biomass to liquid and gaseous products and conversion of cellulosic materials in the biomass to liquid and gaseous products. Hydrogen converts these products to stable materials.

The upflow type is essential so that any solids present in the furnace can be swept up as an upflow feed stream into the quency zone and removed. Char is used as a fuel or feedstock for hydrogen production. If the temperature is too low and/or resistance times are too short, yield of product is lessened. If the temperature is too high and/or resistance time is too long, the products are thermally degraded and give less desirable products. These products are suitable for fuel, but may not be suitable as chemical feedstocks or as liquid transportation fuels. Use of excess oxygen results in production of carbon dioxide. An essential element of the present invention accordingly is control of the oxygen feed to obtain the necessary amount of heat in oxidation zone, and to maintain a temperature within the range of from about 100° C. to 1500° C., i.e., from about 100° C. to about 1500° C. in the preheating zone and from about 200° C. to about 1000° C. in the thermal conversion zone.

By upflow feed stream is meant a stream of feed material flowing upward through the preheating temperature zone wherein biomass and/or extract feed is heated to bring the temperature of the feed up to the necessary temperature for thermal conversion. Preheat temperature can be within the range of from about 100° C. to 1500° C. The heated material flows upward through the terminal conversion temperature zone of about 200° C. to about 1000° C. wherein the products are stabilized and flow upwards with any solids to the quench zone.

The invented process can be carried out in either a batch or continuous type operation. The continuous process is preferred and is as described in the instant specification.

In general, the process of the instant invention in operation is as follows. Biomass which has been chopped or pulverized to a particle size wherein reaction rates fall within specified times, is preheated in a temperature zone of from about 100° C. to about 1500° C. to dry the material, if water is present, and to permit control of the chemical reaction in the thermal conversion zone which follows, thereby obtaining optimum desirable product distribution. The dried biomass is thereupon thermally decomposed in an upflow furnace in an upflow atmosphere of about 200° C. to about 1000° C. followed by a quench. Field-dried whole plants which have been sun-dried to approximately 10–20 (wt)% water can be used. A higher moisture content can be reduced by lengthening the preheat and drying zone. If sun drying is not feasible, suitable drying equipment can be used.

The biomass char serves as fuel or as feedstock for hydrogen production. The excess char and ash are removed following quench by conventional methods such as filters, cyclones or other means. The temperature of the products comprising ethylene and other hydrocarbon gases and liquid condensables with solids is quenched to a temperature less than 400° C. and preferably from about 50° C. to about 300° C. by rapid decrease in pressure while still hot enough to maintain the liquid products in the vapor phase. Solids are removed while the products are still in the vapor phase. The char-free volatile liquids and gas products are transferred to a condenser wherein the condensable liquids and water are removed. The organic liquids and water are separated and the organic liquids are removed for use as they are or for further thermal cracking or upgrading to lower molecular weight hydrocarbons.

An alternative embodiment utilizes solvent extraction of the whole-plant biomass wherein hydrocarbon-containing biomass is chopped or ground to a suitable particle size for solvent extraction. The particles thereupon are percolated in a solvent suitable for solvent extraction such as acetone, butanol, etc. The solvent extract containing hydrocarbon resins is evaporated to dryness, the solvent being recovered. The hydrocarbon resin is thereupon fed to the furnace by a liquid pump. The advantage of using hydrocarbon resin extracts as feed is that the amount of usable chemical feedstock, such as ethylene and propylene, can be increased as is indicated in the following table wherein test results were obtained under a non-reactive gas (helium) to emphasize the different reaction products obtained from plant extracts and dried whole plants. Individual plant biomass can result also in differing results.

| Thermal Conversion of *E. Lathyrus* Plant Extracts and Whole Dried Plants at 850° C. Under Helium | | |
|---|---|---|
| | Acetone Extracts % (wt) | Whole Dried Plants % (wt) |
| Char | 18.4 | 31.5 |
| Liquid | 13.3 | 17.6 |
| Carbon Monoxide | 5.8 | 8.0 |
| Hydrogen | 0.8 | 1.5 |
| Methane | 5.0 | 5.7 |
| Ethylene | 16.7 | 5.0 |
| Ethane | 2.5 | 0.9 |
| Propylene | 5.8 | — |
| Benzene | 4.2 | 1.0 |
| Carbon Dioxide | 27.5 | 27.8 |
| Acetylene | — | 1.0 |
| Total | 100 | 100 |

The raw materials for the process of this invention can be, as stated, the ground or chopped pulverized whole-plant biomass of hydrocarbon-containing plants or the extracted hydrocarbon resins of these plants. The ground or chopped biomass before drying can have a water content varying up to about 95%, the water content of fresh plant materials being about 50 to 95% by weight.

Field-dried materials are preferred for economic reasons. However, if field-dried materials are not available the whole plant biomass can be fed into a drier and the moisture content lowered therein to less than 15 (wt)% and preferably to from 5 to 10 (wt)%. It is not essential to the process of this invention that the materials be completely dry before introduction into the furnace.

Any well known drying implement capable of the requirements of the operation can be used within the scope of the invention. A rotary dryer which can use a portion of the hot gases from carbonization of the char produced by the thermal decomposition process is preferred. This gas can be used to heat the whole plant biomass to a temperature of approximately 100° C. to drive off the contained water.

Accordingly whole-plant biomass or biomass hydrocarbon resin extract is fed into an upflow furnace wherein the preheat temperature is within the range of from about 100° C. to about 1500° C. and wherein controlled thermal conversion at a temperature of from about 200° C. to about 1000° C. takes place. The process preferably uses oxygen rather than air to eliminate need for nitrogen separation from the product.

Control of temperature of the upflow furnace by controlling oxygen input to the oxidation section is essential to the process. Use of a high ratio of oxygen to hydrogen feed creates undesirable conditions within the furnace. With a high oxygen to hydrogen ratio, the thermal conversion temperature can exceed required temperature ranges, the reducing atmosphere is eliminated and production of carbon oxides is maximized. Valuable products are oxidized and an explosive mixture of oxygen and hydrogen can be present. Preferred atmosphere minimizes production of carbon dioxide and maximizes a reducing atmosphere and production of organic liquids and gases suitable as chemical feedstocks and as fuels.

An upflow vertical shaft furnace is preferred in the process of the instant invention. In the upflow vertical shaft furnace, the feed material is fed to the bottom of the furnace by means of a screw conveyer. The upflow material furnace has a preheat zone in the bottom portion and a thermal conversion zone in the upper portion. The feeder compacts the feed passing through the screw feeder, prevents the admittance of air and seals the reactor to maintain positive pressure within the reactor. Generated product gases pass upward through the furnace and are removed from the top of the furnace through a reducing or pressure let-down valve. Temperature control is maintained by monitoring the oxygen and hydrogen ratio with required instrumentation.

Generated product gases and volatile liquids after quench are passed through a cyclone or solids removal means to a condenser in order to trap liquid products. Gaseous products are collected in a container designed for this purpose. The condenser can use commercially available technology with precautions taken to avoid fouling due to tar buildup and with short contact time to stop further chemical reactions.

Plant extracts for which this process can be used include those from the Euphorbiaceae, Asclepiadaceae, Myrtaceae, Apocynaceae, Pinaceae, and Compositae families although the invention is applicable to any plant-derived hydrocarbon resin. Fresh plants are extracted with acetone, cyclohexane, benzene or any other solvent of choice. The solvent is evaporated, recovered and the extracts are thermally converted at temperatures from 200° C. to 1,000° C. Preheating of the extract at temperatures of 100° C. to 1500° C. permits control of the chemical reaction at the thermal conversion temperature which follows, thus obtaining optimum desirable product distribution.

The potential of this recovery method is to obtain gaseous and liquid hydrocarbons such as methane, ethane, ethylene, acetylene, propylene, benzene, as well as hydrogen from plants rich in hydrocarbons. The liquid fraction can be used as is or recycled for further cracking to low molecular weight products or upgraded to products such as gasoline. Carbon dioxide produced in the process can be easily removed from the product stream by conventional absorption technology.

Embodiments of the present invention may be found in the following examples. These embodiments and examples are presented for purposes of illustration only and are not intended to limit the scope of the invention.

EXAMPLE I

The following example simulates an upflow moving bed furnace wherein the feed material progresses through a preheat zone and thence to a thermal conversion zone. The feed material is of the Euphorbiaceae family.

A 10 mg portion of *E. lathyrus* extracted with acetone was ground, placed in a ceramic boat and inserted into a preheating zone at 630° C. for a period of about 5 minutes. The preheating zone comprised a section of a stainless steel tube heated by an electric furnace. A helium gas sweep was used to exclude oxygen. Hydrogen was injected, thereby providing a reducing atmosphere. The simulated thermal conversion zone was heated to 950° C. Vapor residence time (in thermal conversion zone) was 0.4 seconds. Liquid products were trapped in a container cooled with dry ice-acetone and gases were collected in a special plastic container. Analysis was by mass spectrograph. Details are in the following Table I.

TABLE I

| Hydrocarbon Products From Biomass Extract | | | |
|---|---|---|---|
| Run - 4667-69 | 1 | 2 | 3 |
| Wt. - mg | 10.0 | 10.0 | 10.0 |
| Temp. °C. | | | |
| 1 sec. | 655 | 715 | 709 |
| Max. | 810 | 848 | 847 |
| H$_2$, psig | 1510 | 1530 | 1530 |
| VRT - seconds | 0.4 | 0.4 | 0.5 |
| Yield (Wt. %) | | | |
| Methane | 42.4 | 20.2 | 36.4 |
| Ethane | 33.0 | 20.6 | 27.6 |
| Benzene | 9.9 | 5.5 | 1.1 |
| Toluene | 1.8 | 1.0 | 0.9 |
| Propane | Trace | — | 3.6 |

Note:
VRT—Vapor residence time in thermal conversion zone
Wt %-Based on carbon content of feed

EXAMPLE II

The procedure of Example I was repeated using feed material of the Compositae family, an acetone extract of *Grindelia squarrosa*. Results are in Table II.

TABLE II

| Hydrocarbon Products from Biomass Extract | | | | | | | |
|---|---|---|---|---|---|---|---|
| Run No. 4968 | 143-1 | 143-2 | 143-3 | 143-4 | 143-5 | 144-1 | 144-4 |
| Wt - mg | 10 | 10 | 10 | 10 | 10 | 10 | 10 |
| Temp °C. | | | | | | | |
| 1 sec | 690 | 584 | 691 | 793 | 673 | 679 | 733 |
| Max. | 818 | 745 | 775 | 893 | 815 | 821 | 823 |
| H$_2$, psig | 1540 | 1540 | 1560 | 1500 | 1530 | 1520 | 1560 |
| VRT - sec | 0.34 | 0.34 | 0.34 | 0.4 | 0.30 | 0.30 | 0.34 |
| Yield (Wt %) | | | | | | | |
| Methane | 43 | 20.1 | 21.8 | 23.3 | 16.3 | 25.4 | 18.5 |
| Ethane | 23.9 | 9.8 | 23.4 | 15.7 | 20.9 | 15.9 | 23.8 |
| Benzene | 5.1 | 2.6 | 11.3 | 19.7 | 7.2 | 4.9 | 9.3 |
| Toluene | 5.2 | 2.4 | 5.6 | 0.3 | 3.6 | 3.9 | 1.7 |
| Xylene | 2.1 | 1.3 | 7.8 | — | 1.2 | 2.0 | 0.5 |
| Propane | 15.1 | 11.2 | 9.8 | — | 9.4 | 15.2 | 4.5 |
| Butane | Trace | Trace | Trace | — | — | — | 1 |

EXAMPLE III

The procedure of Example I was repeated using feed material of the Euphorbiaceae family, acetone extracts of *E. tirucalli* and *E. marginata*. Results are in Table III.

TABLE III

| Hydrocarbon Products from Biomass Extract | | | | |
|---|---|---|---|---|
| | E. tirucalli | | E. marginata | |
| Run No. 4968 | 21-1-3 | 21-1-4 | 113-1 | 113-2 |
| Wt - mg | 10 | 10 | 10 | 5.2 |
| Temp °C. | | | | |
| 1 sec | 793 | 697 | 830 | 805 |
| Max. | 936 | 809 | 948 | 907 |
| H$_2$, psig | 1520 | 1500 | 1540 | 1540 |
| VRT - sec | 0.34 | 0.30 | 0.34 | 0.30 |
| Yield (Wt %) | | | | |
| Methane | 35 | 41 | 15.4 | 10.9 |
| Ethane | 14 | 14.3 | 15.9 | 8.8 |
| Benzene | 19.0 | 5.8 | 7.9 | 6.8 |
| Toluene | 0.8 | 3.3 | 2.9 | — |
| Xylene | — | 1.0 | — | — |
| Propane | — | 10.2 | — | — |

EXAMPLE IV

The procedure of Example I was repeated using feed material of the Euphorbiaceae family, acetone extracts of *E. lathyrus*. Results are in Table IV.

TABLE IV

| Hydrocarbon Products from Biomass Extract | | | |
|---|---|---|---|
| Run No. 4667-69 | 1 | 2 | 3 |
| Wt - mg | 10.0 | 10.0 | 10.0 |
| Temp °C. | | | |
| 1 sec | 655 | 715 | 709 |
| Max. | 810 | 848 | 847 |
| H$_2$, psig | 1510 | 1530 | 1530 |
| VRT - sec | 0.4 | 0.4 | 0.5 |
| Yield (Wt %) | | | |
| Methane | 34.4 | 18.6 | 30.9 |
| Ethane | 33.0 | 25.3 | 27.6 |
| Benzene | 9.9 | 5.5 | 1.1 |
| Toluene | 1.8 | 1.0 | 0.9 |
| Xylene | — | — | — |
| Propane | Trace | — | 3.6 |

EXAMPLE V

The procedure of Example I was repeated using acetone extracts of resins of the Pinaceae family, a pine tree resin, and of the Apocynaceae family, *Apocynum sibiricum*. Results are in Table V.

TABLE V

| Hydrocarbon Products from Plant Resins | | | | |
|---|---|---|---|---|
| | Pine Tree Resin | | | A. sibiricum |
| Run No. | 4667-1 | 4667-2 | 4667-3 | 4968-136 |
| Wt - mg | 8.5 | 6.6 | 9.9 | 7.1 |
| Temp °C. | | | | |
| 1 sec | 685 | 714 | 721 | 721 |
| Max. | 832 | 859 | 867 | 891 |
| H$_2$, psig | 1530 | 1510 | 1460 | 1540 |
| VRT - sec | 0.5 | 0.34 | 0.34 | 0.66 |
| Yield (Wt %) | | | | |
| Methane | 35.8 | 34.7 | 38.6 | 37.7 |
| Ethane | 40.7 | 25.2 | 35.4 | — |
| Benzene | 11.8 | 8.4 | 14.2 | 1.8 |
| Toluene | 4 | 5.1 | 4.3 | — |
| Xylene | — | 2 | — | — |
| Propane | — | 4 | 7 | — |

EXAMPLE VI

The procedure of Example I was repeated using acetone extracts of *E. heterophylla* of the Euphorbiaceae family. Results are in Table VI.

TABLE VI

| Hydrocarbon Products from Biomass Extract | | |
|---|---|---|
| Run No. 5178 | 101-2 | 101-4 |
| Wt - mg | 2.1 | 10.5 |
| Temp °C. | | |
| 1 sec | 708 | 733 |
| Max. | 916 | 898 |
| H$_2$, psig | 1240 | 1550 |
| VRT - sec | 0.27 | 0.19 |
| Yield (Wt %) | | |
| Methane | 8.9 | 16.6 |
| Ethane | 5.0 | 7.2 |
| Benzene | 3.4 | 1.0 |
| Toluene | 1.5 | 0.6 |
| Xylene | — | — |
| Propane | 1.7 | 5.0 |

EXAMPLE VII

The procedure of Example I was repeated using acetone extracts of *Eucalyptus cineria* of the Myrtaceae family. Results are in Table VII.

TABLE VII

| Hydrocarbon Products from Biomass Extracts | | | |
|---|---|---|---|
| Run No. | 5178-139-2 | 5178-139-3 | 4968-21-1 |
| Wt - mg | 2.4 | 38.2 | 10.0 |
| Temp °C. | | | |
| 1 sec | 696 | 744 | 720 |
| Max. | 866 | 935 | 879 |
| $H_2$, psig | 1310 | 1510 | 1300 |
| VRT - sec | 0.27 | 0.19 | 0.27 |
| Yield (Wt %) | | | |
| Methane | 13.5 | 16.5 | 46.3 |
| Ethane | 10.3 | 4.2 | 19.1 |
| Benzene | 1.2 | 1.0 | 4.2 |
| Toluene | 0.9 | 0.5 | 4.0 |
| Xylene | — | — | 2.0 |
| Propane | 7.3 | 4.0 | 16.0 |

What is claimed is:

1. A process which comprises hydropyrolysis in gas phase of hydrocarbon containing whole plant biomass for production of fuel gases and organic liquids suitable for use as hydrocarbon fuels and as chemical feedstocks which process comprises:
   (a) feeding chopped whole plant biomass feed of a suitable particle size by means of feed inlet ports to a furnace containing an oxidation zone, a preheat zone and a thermal conversion zone wherein said furnace is an upflow furnace and means are provided for exclusion of oxygen-containing gases from said feed inlet ports,
   (b) injecting hydrogen at a pressure within the range of from 2 to 100 atmospheres into a burner grid of said oxidation zone and said preheat zone,
   (c) injecting a limited amount of an oxygen-containing gas into said burner grid of said oxidation zone at a pressure of from about 1 to 100 atmospheres, wherein the ratio of oxygen to hydrogen is within the range of from about 1:2 to 1:100, moles of oxygen to moles of hydrogen, so that a hydrogen-oxygen reaction takes place,
   (d) injecting said biomass feed into said preheat zone to heat said biomass feed to a temperature suitable for thermal conversion, excess hydrogen being present at sufficient pressure to provide an upflow draft, thereby transporting said biomass feed from said preheat zone wherein the preheat zone temperature is in the range of from 100° C. to 1500° C. to said thermal conversion zone wherein a reducing atmosphere is present at a thermal conversion zone temperature of from 200° C. to about 1000° C. and a pressure of from 2 to 100 atmospheres,
   (e) exposing said transported biomass feed in said thermal conversion zone to said thermal conversion zone temperature for a period of 0.1 second to one minute so that the biomass is hydropyrolyzed,
   (f) removing biomass products and unconverted mass from said thermal conversion zone to a pressure-reducing quench vessel wherein pressure is reduced and temperature of said biomass products and the unconverted biomass feed is reduced to a temperature less than 400° C.,
   (g) removing solids from said biomass products,
   (h) recovering liquid condensibles and generated product gases from the biomass products.

2. The process of claim 1 wherein said oxygen-containing gas is molecular oxygen.

3. The process of claim 1 wherein the said biomass comprises hydrocarbon-containing plants selected from the group of plant families consisting of Euphorbiaceae, Asclepiadaceae, Myrtaceae, Apocynaceae, Pinaceae and Compositae families.

4. The process of claim 3 wherein said hydrocarbon-containing plants are selected from the group consisting of *Euphorbia heterophylla, Euphorbia lathyrus, Euphorbia marginata, Asclepias syriaca, Asclepias tuberosa, Calotropis procera, Apocynum sibiricum, Grindelia squarrosa, Eucalyptus cineria* and *Euphorbia tirucalli.*

5. A hydropyrolysis process in gas phase for production of fuel gases and organic liquids suitable for use as hydrocarbon fuels and as chemical feedstocks from hydrocarbon-containing biomass which process comprises:
   (a) grinding or chopping hydrocarbon-containing biomass to a particle size suitable for solvent extraction,
   (b) percolating said particles in a solvent suitable for hydrocarbon extraction to form a solvent extract of said hydrocarbon-containing biomass,
   (c) evaporating and recovering solvent from said solvent extract to obtain hydrocarbon resin extract,
   (d) feeding said hydrocarbon resin extract by means of feed inlet ports to an upflow furnace containing an oxidation zone, a preheat zone and a thermal conversion zone wherein means are provided for exclusion of oxygen-containing gases from said feed inlet ports,
   (e) injecting hydrogen at a pressure within the range of from about 2 to 100 atmospheres into a burner grid of said oxidation zone and said preheat zone,
   (f) injecting a limited amount of an oxygen-containing gas into said burner grid of said oxidation zone at a pressure of from about 1 to about 100 atmospheres, wherein the ratio of oxygen to hydrogen is within the range of from about 1:2 to 1:100, moles of oxygen to hydrogen, so that a hydrogen-oxygen reaction takes place,
   (g) injecting said hydrocarbon resin extract feed into said preheat zone wherein temperature is in the range of from 100° C. to 1500° C. to heat said extract feed to a temperature suitable for thermal conversion, excess hydrogen being present at sufficient pressure to provide an upflow draft, thereby transporting said extract feed from said preheat zone to said thermal conversion zone wherein a reducing atmosphere is present at a thermal conversion temperature of from about 200° C. to about 1000° C. and a pressure of from about 2 to 100 atmospheres,
   (h) exposing said transported resin extract feed in said thermal conversion zone to said thermal conversion temperature for a period of 0.1 second to one minute so that the extract is hydropyrolyzed,
   (i) removing extract products and unconverted resin extract feed from said thermal conversion zone to a pressure-reducing quench vessel wherein pressure is reduced and temperature of said extract products and the unconverted resin extract feed is reduced to a temperature less than 400° C.,
   (j) recovering liquid condensibles and generated product gases from the extract products.

6. The process of claim 5 wherein said oxygen-containing gas is molecular oxygen.

7. The process of claim 5 wherein said hydrocarbon-containing biomass comprises hydrocarbon-containing plants selected from the group of plant families consisting of Euphorbiaceae, Asclepiadaceae, Myrtaceae, Apocynaceae, Pinaceae and Compositeae families.

8. The process of claim 7 wherein said hydrocarbon-containing plants are selected from the group consisting of *Euphorbia heterophylla, Euphorbia lathyrus, Euphorbia marginata, Asclepias syriaca, Calotropis procera, Apocynum sibiricum, Grindelia squarrosa, Euphorbia tirucalli, Asclepias tuberosa* and *Eucalyptus cineria*.

* * * * *

UNITED STATES PATENT OFFICE
CERTIFICATE OF CORRECTION

Patent No. 4,364,745     Dated December 21, 1982

Inventor(s) Thomas A. Weil

It is certified that error appears in the above-identified patent and that said Letters Patent are hereby corrected as shown below:

Col.    Line 10     7     "material furnace" should read --vertical furnace

Signed and Sealed this

Twenty-eighth Day of June 1983

[SEAL]

Attest:

GERALD J. MOSSINGHOFF

Attesting Officer     Commissioner of Patents and Trademarks